(12) United States Patent
Flashinski et al.

(10) Patent No.: US 6,360,477 B1
(45) Date of Patent: Mar. 26, 2002

(54) INSECT CONTROL POUCH

(75) Inventors: Stanley J. Flashinski, Racine, WI (US); Bruno W. Fricke; Edgar Pohlmann, both of Rio de Janeiro (BR); Murthy S. Munagavalasa, Racine; Michael J. Skalitzky, Kenosha, both of WI (US)

(73) Assignee: S. C. Johnson & Son, Inc, Racine, WI (US)

( * ) Notice: Subject to any disclaimer, the term of this patent is extended or adjusted under 35 U.S.C. 154(b) by 0 days.

(21) Appl. No.: 09/619,118

(22) Filed: Jul. 19, 2000

(51) Int. Cl.[7] .................................................. A01M 1/20
(52) U.S. Cl. ............................ 43/131; 43/107; 223/86
(58) Field of Search ..................... 43/131, 107; 223/86; 512/4

(56) References Cited

U.S. PATENT DOCUMENTS

| | | | |
|---|---|---|---|
| 3,655,129 A | * 4/1972 | Seiner | 239/60 |
| 4,145,001 A | 3/1979 | Weyenberg, et al. | 239/56 |
| 4,158,440 A | 6/1979 | Sullivan, et al. | 239/1 |
| 4,720,417 A | * 1/1988 | Sweeny et al. | 428/201 |
| 5,164,178 A | * 11/1992 | Muysson | 424/76.4 |
| 5,487,932 A | 1/1996 | Dunshee | |
| 5,637,401 A | * 6/1997 | Berman et al. | 252/315.2 |
| 5,961,043 A | 10/1999 | Samuelson, et al. | 239/54 |

FOREIGN PATENT DOCUMENTS

DE     0081791 A1  *  6/1982

OTHER PUBLICATIONS

U.S. application No. 09/326,446, Munagavalasa, filed Jun. 4, 1999.

* cited by examiner

Primary Examiner—Peter M. Poon
Assistant Examiner—F C Copier

(57) ABSTRACT

Disclosed herein is an article (such as an insect control pouch) to dispense a volatile active (such as an insect control agent). The pouch is formed from a single layer polymeric non-absorbing film. The pouch traps the active until use of the pouch is desired. When the pouch is opened the walls of the pouch serve as a substrate from which the active can readily passively evaporate. Methods of forming such pouches using heat sealing techniques, and methods of using such pouches, are also disclosed.

4 Claims, 3 Drawing Sheets

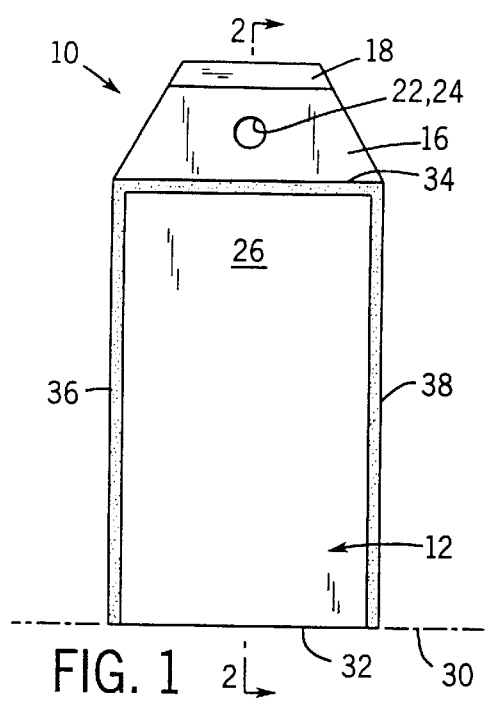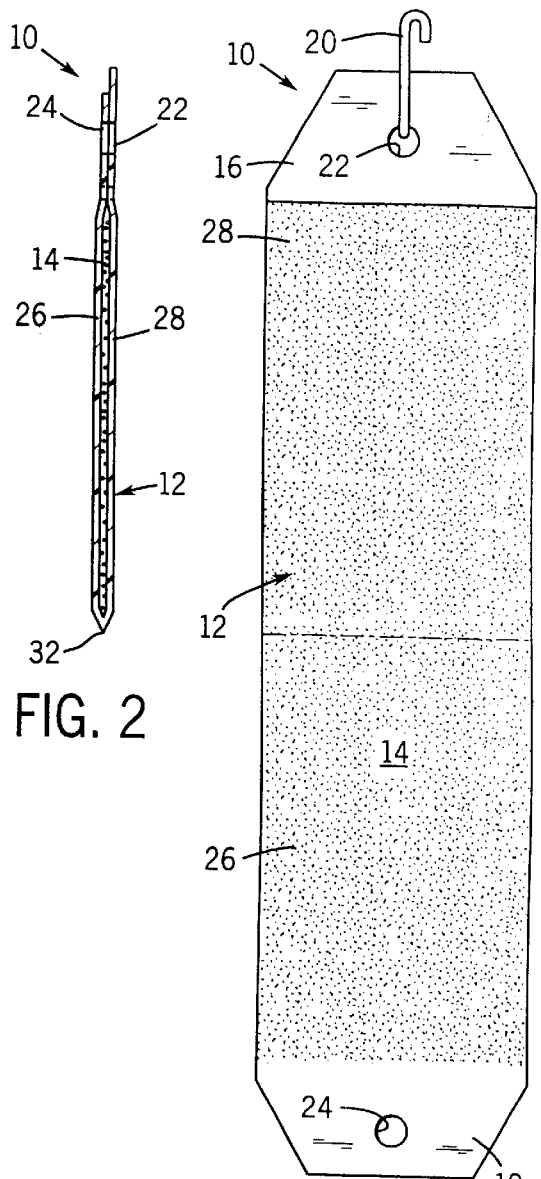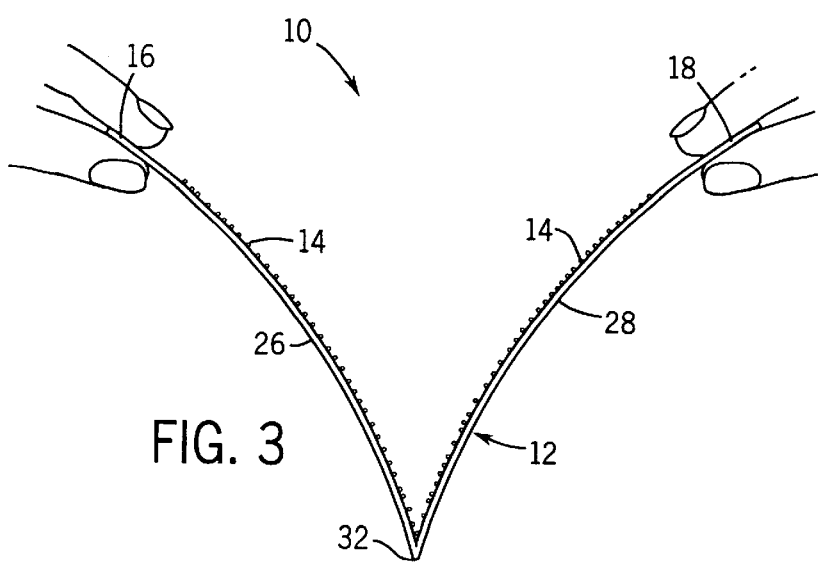

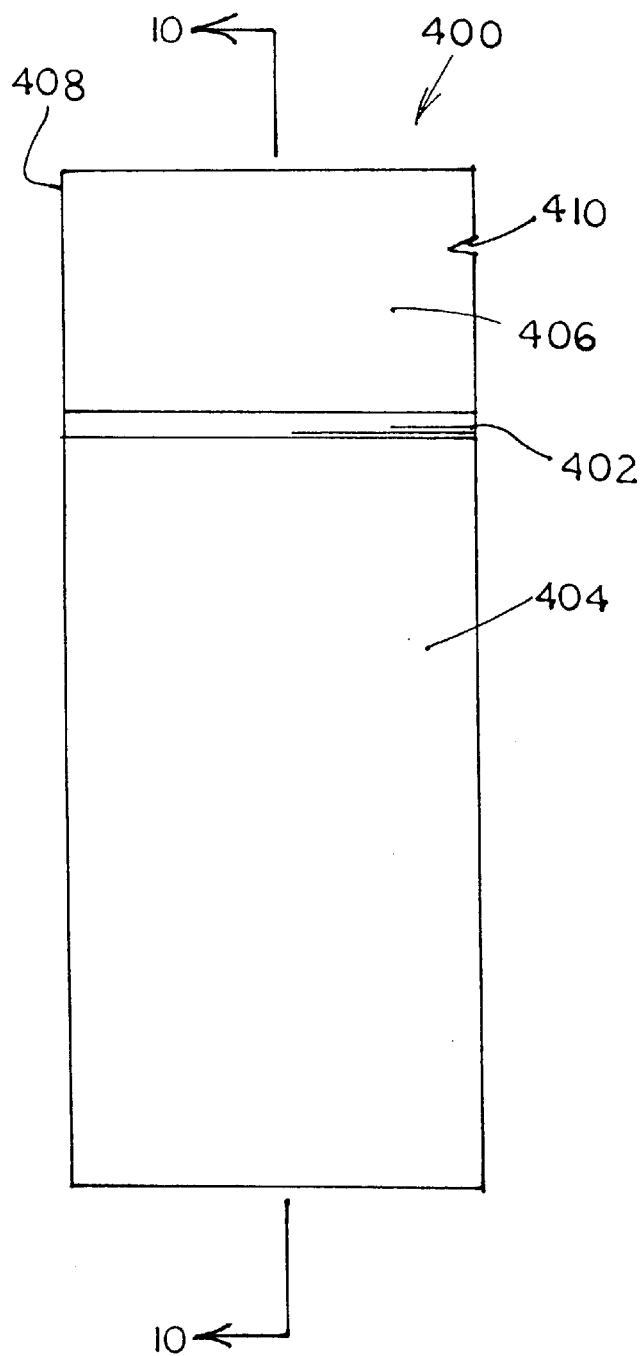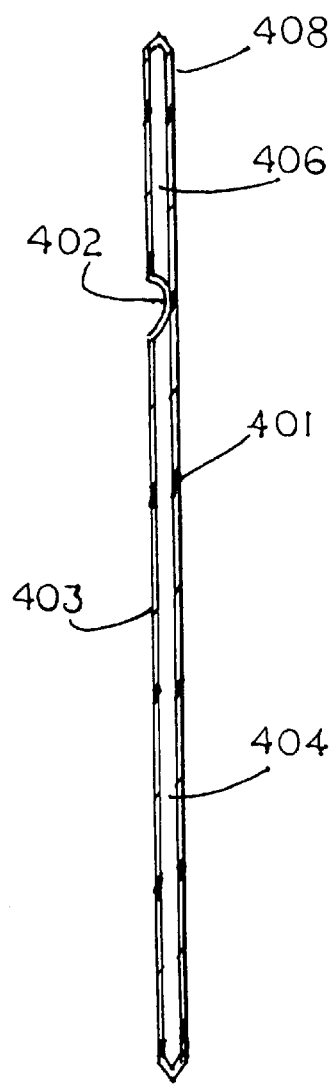
Fig. 9
Fig. 10

INSECT CONTROL POUCH

CROSS REFERENCES TO RELATED APPLICATIONS

Not applicable

STATEMENT REGARDING FEDERALLY SPONSORED RESEARCH

Not applicable

BACKGROUND OF THE INVENTION

The present invention relates generally to dispersing actives into the air. It appears especially well suited to disperse insect control actives such as insect repellants and insecticides to control flying insects that may be present in indoor rooms.

It is beneficial to control flying insects within buildings. Insect control is also useful in other areas, including screened areas such as tents, that are subject to invasion by flying insects.

Devices that dispense insecticide vapors to control insects in such settings traditionally require heating or burning a liquid or solid to disperse the active ingredients. Products that use a heat source may require a safe burning site, e.g. in the case of insect coils, or may require a source of electrical current for typical heated evaporation products.

Thus, techniques have been designed to dispense such insect control actives (and other actives such as fragrances and deodorizers) by employing passive evaporation, i.e. evaporation without the application of heat. For example, WO96/32843 describes an insect strip to control flying insects, the strip having a substrate that is impregnated with an active ingredient available for passive evaporation. The active ingredient is selected from transfluthrin, prallethrin, vapothrin, tefluthrin, esbiothrin, dichlovos (DDVP), and combinations thereof.

Co-pending U.S. patent application Ser. No. 09/326,446, filed Jun. 4, 1999, assigned to the assignee of the present invention, discloses insect control ingredients that can passively evaporate from non-absorbing substrate strips (such as those made of Barex® polymeric film) to control flying insects. The disclosures of this patent application and all other patent applications, patents, and publications referred to herein are incorporated by reference as if fully set forth herein.

The vaporizable active ingredients of the aforementioned insect control devices are typically stored for shipment, sale, and home storage in some type of separate, tear open, vapor impermeable pouch or other container. The pouch or other container prevents the active ingredient from prematurely evaporating before insect control is required and also provides a way of avoiding having those handling the device accidentally contact the active during such non-use situations. Thus, in the past, both a substrate from which the active could passively vaporize and a sealed barrier pouch or container were needed. See also U.S. Pat. No. 5,487,932.

However, this added material and assembly cost money. This is a significant problem, because these devices are often intended for use in areas of the world where the average income is exceedingly low while, at the same time, the rate of malaria and other flying insect borne disease is high. Thus, a need exists for developing ways to reduce the cost of such passive evaporation strips while still providing the functions of both a dispensing substrate and a sealed pouch or container for that substrate prior to its being needed for use.

BRIEF SUMMARY OF THE INVENTION

In one embodiment, the invention provides an article to dispense a vaporizable active selected from the group consisting of insect control ingredients and fragrances, deodorizers, and other air modification volatile ingredients. The article has a pouch with opposed and, preferably, single layer walls that are releasably sealed together to define an interior cavity therebetween. An inside surface of at least one of the walls is coated with a vaporizable active. The term "coated" is herein defined to include all means of surface treating such that a surface carries the material with which it is coated. The pouch is impermeable to the active contained therein and has an outside, exposed surface. Preferably, no separable, active-bearing article is contained within the pouch with, instead, the inside surfaces of the pouch being the only structure of the article coated with the vaporizable active.

In preferred embodiments, the pouch is formed by folding a strip of polymeric film upon itself, with the fold constituting a first side of the pouch. The remaining sides are releasably sealed. Preferably the pouch is generally rectangular, having the folded side and three remaining, sealed sides. Alternatively, two sheets of the film could be placed on each other and then sealed on all sides, again preferably in rectangular shape with four, sealed sides. For ease of description, and unless a contrary meaning is clearly intended in the context, pouches or sheets of material will be referred to has having four "sides" even if their shape is actually rounded, irregular, or has in literal fact more than four sides, the reference to a shape having four sides simply intended to describe a closed figure. Thus, a circle, oblong, square, triangle, pentagon, or other closed figure will be equally referred to as figures having "four sides."

The sealing is preferably heat sealing, such as hot wire sealing or sealing using a heat sealing bar, preferably the sealing bar being 0.5 mm–2.5 mm wide. A narrow, hot seal is desirable for creating a vapor-tight seal. If only a liquid-tight seat is desired, as will be discussed below, a broader seal width created with a cooler sealing device is preferable.

The pouch can have, extending from its end, a portion that is free of the active, which portion has a through hole or is in the form of a hanger. Alternatively or additionally, the extending portion can be in the form of a pair of unsealed flaps extending from the opposed walls at a sealed side of the pouch to form tabs extending beyond the point of sealing to facilitate the opening of the pouch. If desired, the flaps can be of different sizes, and one of the flaps can include a through hole.

The interior surface of the pouch can be textured, corrugated, or otherwise modified to increase its surface area, thus providing the ability to hold a greater amount of volatile active than would otherwise be the case, extending the time over which volatile remains to be released from an opened pouch.

In a preferred embodiment, the pouch is subdivided by an intermediate seal into two chambers, the remaining margins of both chambers being sufficiently sealed as to prevent passage of the volatile active even when in vapor form. At least one interior surface of a first of the two chambers is coated with the volatile active to be dispensed. In contrast, the interior surfaces of the second, remaining chamber are free of any such coating of volatile active. The end of the second chamber remote from the intermediate seal is tearable to allow a user to open the second chamber to grasp the opposed walls thereof to then part the intermediate seal and expose the interior surfaces of the first chamber. It will be apparent that this arrangement allows a user to tear open the first chamber while avoiding having to touch any volatile active-coated surface.

Sometimes an intermediate seal made sufficiently complete to contain volatile active even in vapor form also is mechanically strong enough that a user can tear the pouch walls before the intermediate seal opens, resulting in an unreliably openable product. To avoid this, in the most preferred embodiment, the intermediate seal is made adequate to prevent the passage therethrough of the volatile active when it is in liquid or solid form, even though it may not be adequate to prevent the passage of active in vapor form. This lesser sealing requirement allows the intermediate seal to also be sufficiently releasable that the intermediate seal opens without any tearing of the opposed walls. Vapor is contained within the second chamber by the vapor-tight seal around its remaining margins. This arrangement provides a reliably openable article that remains vapor tight.

Preferably the opposed walls at a sealed margin of the second chamber at a location remote from the intermediate seal include a notch that provides a point of mechanical weakness to make easier a user's tearing open the end of the second chamber. While a wide variety of vaporizable insecticides, repellants, and insect growth regulators may be suitable insect control ingredients, it is highly desirable for insect control purposes that the control agent be selected from the group consisting of transfluthrin, tefluthrin, prallethrin, vapothrin, esbiothrin, dichlovos, and combinations thereof.

Preferred materials for forming the pouch are 1.0 mm to 3.0 mm thick films of acrylonitrile methacrylate copolymer, polyester, polyvinyidene chloride, orientated polyethylene, nylon, polyvinyl alcohol, orientated polypropylene, and ethylene vinyl alcohol. They are all vapor impermeable, heat sealable, and provide suitable relatively non-absorbent surfaces that can be coated with the active. Alternatively, laminated or otherwise layered films can be used, including multi-layered films in which individual layers provide only some but not all such features as barrier strength, sealability, an active release surface that can be coated with an active without absorbing or chemically reacting with it. For example, strong films that would not be good active release surfaces can be metallized or combined with a metal foil layer that can thus provide a release surface. Sealant layers can include such materials as, for example, polypropylene, polyethylene, polyethylene tetephthalate-based films, and ethyl vinyl alcohol.

Most preferably, the insect control ingredient is transfluthrin, and the walls are formed of a modified acrylonitrile methacrylate copolymer such as the material sold as Barex® 210 or Barex® 218 (both available from BP Chemicals/Amoco).

A further form of the invention is a method of forming such a pouch where one obtains a pocket formed of polymeric film, injects a selected active in the pocket, and so heat seals the pocket as to form an enclosed pouch with the active releasably trapped therein.

In another form, the invention provides a method of controlling flying insects. One obtains one of the above articles, opens the pouch to form a strip, and then hangs the strip in a selected environment such that an insect control ingredient can vaporize into the environment.

In yet another form, the invention provides an alternative embodiment of the method of forming such a pouch. One obtains a polymeric film, coats a surface of the film with the active, folds the film upon itself so that the coated surface is an inward surface, and heat seals at least three peripheral sides of the resulting structure to form an enclosed pouch with active releasably trapped therein.

In still another form, the invention provides a further alternative embodiment of the method of forming such a pouch. One obtains two sheets of polymeric film, coats a surface of at least one of the sheets with the active, places the sheets upon each other so that said surface faces the other sheet, and heat seals peripheral sides of the resulting structure to form an enclosed pouch with the active releasably trapped therein.

It will be appreciated from the discussion herein that the inventors of the present invention have identified vapor impermeable, releasably sealable materials that are also suitable to be a substrate for an active insect control ingredient. The present invention thus avoids the need for a separate pouch to house the coated substrate.

Preferably, hot knife and bar heat sealing processes are used to releasably seal the pouch. In this way, the pouch can be hermetically sealed to prevent the insect control ingredient from escaping during storage, but can be easily peeled apart for use.

Another advantage is that the strip substrate can be formed to have a free end extending from one end of the pouch, that free end being kept free of the insect control ingredient and thus being available to be handled by a user to open the pouch or hang the strip substrate without having to contact the insect control ingredient.

The present invention thus provides a very low-cost vapor dispersing article wherein the strip substrate acts as a base for the vaporizable active and also forms the sides of a vapor impermeable pouch.

These and still other advantages of the invention will appear from the following description. In the description reference is made to the accompanying drawings which from a part hereof and in which there is shown by way of illustration preferred embodiments of the invention. However, the claims should be looked to in order to judge the full scope of the invention.

BRIEF DESCRIPTION OF THE DRAWINGS

FIG. 1 is a front elevational view of a preferred pouch of the present invention;

FIG. 2 is a side cross-sectional view of the pouch of FIG. 1;

FIG. 3 is an end view showing the FIG. 1 pouch in the process of being peeled open for use;

FIG. 4. is a front elevational view showing the FIG. 1 pouch with a hanger inserted at its upper end, and having the pouch opened;

FIG. 9 is a fifth embodiment having an intermediate seal.

FIG. 10 is a cross-sectional view of the embodiment of FIG. 9 taken along section lines 10—10 of FIG. 9.

DETAILED DESCRIPTION OF THE PREFERRED EMBODIMENT

Figure 5:
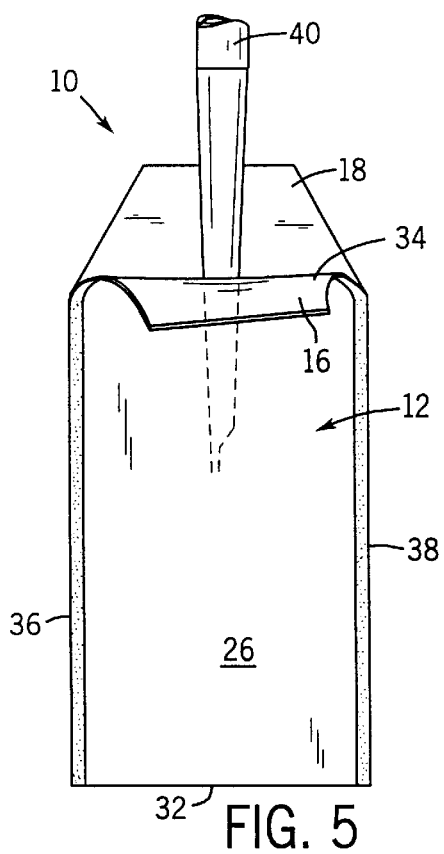
FIG. 5 shows an envelope into which insect control ingredient is being dispensed prior to completing the sealing of the pouch.

Referring to the first page of drawings, pouch 10 of the present invention is formed from a polymeric film substrate 12 that is coated on a side (inside surfaces of one or both opposed walls 26 and 28) with insect control ingredient 14 dissolved in a solvent.

The preferred insect control active 14 is transfluthrin ((IR-trans)-(2,3,5,6-tetrafluorophenyl) methyl 3-(2,2-dichoroethenyl)-2,2-dimethyl cyclopropane carboxylate—also called Bayothrin or NAK 4455). Transfluthrin is effective at low concentrations against flying insects, particularly mosquitoes, flies, cockroaches, and moths, and has sufficient volatility to attain these low but effective concentrations at typical room temperatures. Its extremely rapid knock-down property, even at very low concentrations and application rates, makes this chemical particularly suitable for passive evaporation insect control devices.

The active ingredient 14 may be other suitable actives as well, such as pyrethrum and pyrethroid type materials commonly used in mosquito coils. As alluded to above, these actives include d-allethrin, allethrin, prallethrin, bioallethrin, s-bioallethrin, esbiothrin, dichlorvos, transfluthrin, tefluthrin, vapothrin, and combinations thereof. Other suitable insect control actives include the repellants DEET, citronella, lemon grass oil, lavender oil, cinnamon oil, neem oil, clove oil, sandalwood oil and geraniol as well as the insect growth regulators, such as hydroprene. Combinations of such ingredients are also possible.

The solvent is preferably a hydrocarbon solvent, such as Isopar, owing to the ability of such solvents to solubilize the active ingredient and permit uniform distribution of the active ingredient on the substrate without adversely affecting the substrate. Such solvents also volatilize rapidly without substantially volatilizing the active ingredients. Other solvents known for use with such volatiles may also be used.

The substrate 12 must be made of a material capable receiving and holding the active ingredient and readily releasing it by passive evaporation. The substrate 12 should also be inert and essentially non-absorbing (preferably having a solubility less than 40 $\mu g/cm^2$) so as to provide low resistance to the diffusion of the active ingredient into the ambient air. The substrate 12 must also be vapor impermeable and hermetically sealable.

A preferred substrate material is a acrylonitrile methacrylate copolymer film, such as Barex® 210 and 218 available from BP Chemicals/Amoco. Other suitable non-absorbing polymeric films include, without limitation, polyester, polyvinylidene chloride e.g. Saran, orientated high density polyethylene, nylon, polyvinyl alcohol, orientated polypropylene, and ethylene vinyl alcohol.

The substrate 12 is preferably a thin strip having flaps 16 and 18 at its ends that are free of the active ingredient 14, with flap 18 being truncated so that the flaps 16 and 18 are of different sizes. Flaps 16 and 18 also have through holes 22 and 24, which provide locations for attaching a hanger 20, as shown in FIG. 4. If desired, only one such hole need be formed. Examples of suitable hanger 20 and other attachment means include hooks, strings, magnetic clips, clamps, hook and loop fasteners, mechanical clips and fasteners, adhesives, and the like. A preferred fastener arrangement includes adhesive strips attached to one or both flaps, with holes or ties provided in or for attachment to the strips. Any such means provided on the substrate should not substantially block the passage of air over the substrate.

As best seen in FIGS. 1 and 2, the pouch 10 has front 26 and back sides 28 with the facing surfaces coated with the active ingredient 14 to define a cavity between the opposed walls. Preferably, the substrate 12 is folded in two along a fold line 30 slightly off the mid-point of the substrate 12 so that the back side flap 18 extends past the front side flap 16. Each side 26 and 28 share a common bottom 32 and a top 34 and lateral 36 and 38 edges are initially open prior to being sealed.

The lateral edges 36 and 38 can then be sealed, preferably using a releasable sealing technique, such as pressure sealing, heat sealing, or ultrasonic welding. In any case, the seal must be a vapor impermeable seal. Other sealing techniques can be used, such as using a pressure sensitive adhesive.

Note also that is possible for the front 26 and back 28 sides to initially be two separate pieces of substrate. In that case, the films would be placed on each other and need to be also sealed at the bottom.

Referring now to FIG. 5, at this point the substrate 12 is in the form of a pocket having an opening at the top 34. Any effective conventional method may be used to coat the substrate 12 with the active ingredient 14. The substrate 12 is preferably coated with the active ingredient by dissolving an appropriate amount of the active ingredient in a hydrocarbon solvent and thoroughly wetting the pouch 10 interior by injecting the solvent into the pocket, for example through tip 40 of an applicator. In this manner, no active ingredient 14 contacts the flaps 16 and 18. At this point, the top of the pocket can be heat sealed to form the pouch.

Such pouches 10 can be formed using high speed automation equipment. Multiple insect strips can be cut from a self-wound reel of the substrate at a width equal to the unfolded length of the substrate 12. Then multiple strips can be simultaneously folded lengthwise.

Alternatively, and probably preferably, the cuts can be made after the initial folding, using a hot knife or wire sealing technique. In this manner, the folded substrate can simultaneously be heat sealed and cut at the sides' edges. As described above and shown in FIG. 5, the active ingredient can then be added to each envelope through the opening at the top which is then bar heat sealed. A hanger hole is provided and corners of the flaps are cut for aesthetics. Alternatively, prior to cutting, the inside surface of the pre or post folded length of substrate can be coated with the active ingredient before the cutting and sealing steps.

In either case the preferred conditions for a Barex® film coatable with transfluthrin are that the sealing be conducted with a 1.3 second dwell time at 80 psi and 150–175° C.

Referring now to FIG. 3, the pouch 10 can be activated by grasping flaps 16 and 18, and pulling in generally opposite directions until the top 34 and side edge 36 and 38 seals are broken and the substrate 12 is unfolded as shown in FIG. 4. The hanger 20 may be inserted into either of the through holes 22 and 24 and the resulting strip can be suspended by a suitable hook, bar or ledge (e.g. on a closet clothes bar).

Strips of the present invention can be placed in any environment where there is some air movement passing over the coated side of the substrate 12, thereby allowing the active ingredient 14 to continuously passively evaporate into the atmosphere for an extended period of time. Suitable environments include enclosed rooms as well as volumes of open air space, such as patios, and the like. Preferably the invention is used to control mosquitoes, but it may also be used to control a wide variety of other flying insects by suitable selection of the insecticide or repellant.

Figure 6:
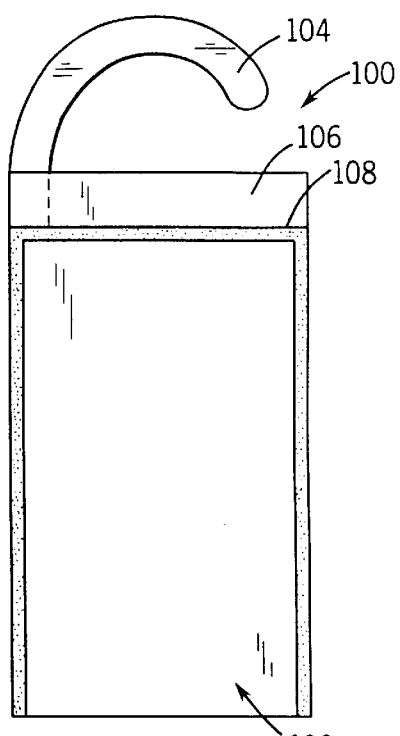
FIG. 6 is a second embodiment where the upper extending portion of the FIG. 1 embodiment has been replaced by a hanger.

Referring now to FIG. 6, an alternate embodiment 100 is shown where substrate 102 is cut to define a hanger portion 104. A smaller flap 106 integral with the front side of the pouch extends past the top seal 108. The pouch is opened by grasping the hanger 104 and the flap 106 pulling in opposing directions, as described above. Once opened, the insect strip can be suspended by the hanger 104.

Figure 7:
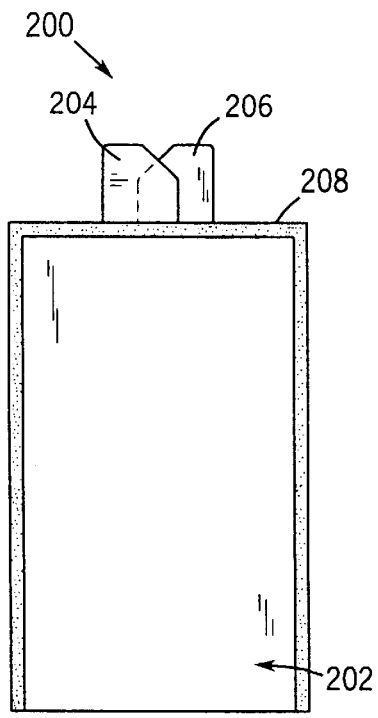
FIG. 7 is a third embodiment having integral grip tabs extending from each pouch wall.

Referring next to FIG. 7, a second alternate embodiment 200 has substrate 202 cut or augmented so that when the pouch is formed a pair of grip tabs 204 and 206, for unfolding the pouch, extend in non-overlapping fashion from the top seal 208 of the front and back sides of the pouch. The grip tabs 204 and 206 can be integral with the substrate 202. Or, the grip tabs 204 and 206 can be sealed or adhered to the substrate 202 at the top seal 208. Although not shown, a hanger attachment location, such as a through hole, could be provided at one or both of the grip tabs.

Figure 8:
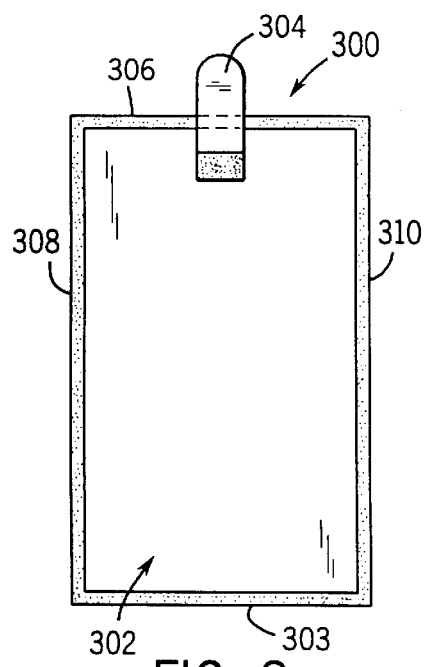
FIG. 8 is a fourth embodiment having separately attached grip tabs at the front and back sides of the pouch.

FIG. 8 shows yet another alternate embodiment 300, in which the substrate 302 is formed from two separate film sheets placed one on top of another. All four edges (including bottom 303) are sealed using a sealing process. Two grip tabs 304 (one shown) are adhered to the front and back sides for separating the top 306 and lateral seals 308 and 310. The adhesive used to attach these must create a stronger bond than the heat seal along the top and sides of the pouch. As with the embodiment of FIG. 7, a hanger attachment location, such as a through hole, could be provided at one or both of the grip tabs 304.

FIGS. 9 and 10 show yet another alternative embodiment, pouch 400, preferred for its ability to be opened reliably, without tearing problems that can occur in other embodiments. Corresponding with the previous embodiments, the pouch 400 has opposed walls 401,403 but is also subdivided by an intermediate seal 402 into first and second chambers 404,406. The remaining margins of both chambers are sufficiently sealed as to prevent passage of the volatile active even when in vapor form. As in the embodiments previously discussed, at least one interior surface of the first 404 of the two chambers is coated with the volatile active to be dispensed. In contrast, the interior surfaces of the second chamber 406 are free of any such coating of volatile active.

The end 408 of the second chamber 406 remote from the intermediate seal 402 is tearable to allow a user to open the second chamber and grasp the opposed walls thereof to then part the intermediate seal 402 and expose the interior surfaces of the first chamber 404. It will be apparent that this arrangement allows a user to tear open the first chamber 404 while avoiding having to touch any volatile active-coated surface.

Sometimes an intermediate seal made sufficiently complete to contain volatile active even in vapor form also is mechanically strong enough that a user can tear the pouch walls before the intermediate seal opens, resulting in an unreliably openable product. To avoid this, in the most preferred embodiment, the intermediate seal 402 is made adequate to prevent the passage therethrough of the volatile active when it is in liquid or solid form, even though it may not be adequate to prevent the passage of active in vapor form, This lesser sealing requirement allows the intermediate seal 402 to also be sufficiently releasable mechanically that the intermediate seal opens without any tearing of the opposed walls 401,403. Vapor is contained within the second chamber 406 and within the entire pouch 400, by the vapor-tight seal around the remaining margins of the first and second chambers 404,406. This arrangement provides a reliably openable article that remains vapor tight. Preferably the opposed walls at a sealed margin of the second chamber 406 at a location remote from the intermediate seal 402 include a notch 410 that provides a point of mechanical weakness to make easier a user's tearing open the end of the second chamber.

While a wide variety of vaporizable insecticides, repellants, and insect growth regulators may be suitable insect control ingredients, it is highly desirable for insect control purposes that the control agent be selected from the group consisting of transfluthrin, tefluthrin, prallethrin, vapothrin, esbiothrin, dichlovos, and combinations thereof.

It should be appreciated that the active dispensing articles of the present invention could be formed in still other embodiments. These are also intended to be within the scope of the present invention. For example, the active can instead (or also) be a fragrancer/deodorizer, using any of a wide variety of such volatiles known in the art (e.g. citronella, limonene, eucalyptus). Accordingly, the claims should be referenced in order to determine the full scope of the invention.

INDUSTRIAL APPLICABILITY

The invention provides a hangable strip allowing for passive evaporation of an active ingredient, in which no separate outer layer or envelope is required.

What is claimed is:

1. An article to dispense a volatile active, comprising a pouch having opposed walls made of a ploymeric material, each wall having only one layer, where said walls are releasably sealed together to define an interior cavity therebetween, the walls thus having inside surfaces within the pouch and outside, exposed surfaces, the walls and seals being impermeable to the active, an inside surface of at least one of said walls being coated with the vaporizable active, wherein no separable, active-bearing article is contained within the pouch.

2. An article to dispense a volatile active, comprising a pouch having opposed walls that are releasably sealed together to define an interior cavity therebetween, the walls thus having inside surfaces within the pouch and outside exposed surfaces, the walls and seals being impermeable to the active, an inside surface of at least one of said walls being coated with the vaporizable active, wherein an interior surface of the pouch is textured or corrugated to increase its surface area, thus providing the ability to hold a greater amount of volatile active than would otherwise be the case, extending the time over which volatile remains to be released from an opened pouch.

3. An article to dispense a volatile active, comprising a pouch having opposed walls that are releasably sealed together to define an interior cavity therebetween, the walls thus having inside surfaces within the pouch and outside, exposed surfaces, the walls and seals being impermeable to the active, an inside surface of at least one of said walls being coated with the vaporizable active, wherein the pouch is subdivided by an intermediate seal into two chambers, the remaining margins of both chambers being sufficiently sealed as to prevent passage of the volatile active even when in vapor form, at least one interior surface of a first of the two chambers being coated with the volatile active to be dispensed while the interior surfaces of the second, remaining chamber are free of any such coating of volatile active, the end of the second chamber remote from the intermediate seal being tearable to allow a user to open the second chamber to grasp the opposed walls thereof to then part the intermediate seal and expose the interior surfaces of the first chamber, the intermediate seal being adequate to prevent the passage therethrough of the volatile active when in liquid or solid form while also being sufficiently releasable that the intermediate seal opens without any tearing of the opposed walls.

4. The article of claim 3 wherein the opposed walls at a sealed margin of the second chamber at a location remote from the intermediate seal include a notch that provides a point of mechanical weakness to make easier a user's tearing open the end of the second chamber.

* * * * *